United States Patent [19]

Litt et al.

[11] Patent Number: 5,102,996
[45] Date of Patent: Apr. 7, 1992

[54] DNA PROBE WHICH REVEALS A HYPERVARIABLE REGION ON HUMAN CHROMOSOME 19

[76] Inventors: Michael Litt, 3865 N.E. Klickitat, Portland, Oreg. 97212; Linda L. Bufton, 2270 Lombard, North Bend, Oreg. 97459; Norman E. Buroker, 21617 88th Ave., W., Edmonds, Wash. 98020

[21] Appl. No.: 53,320

[22] Filed: May 22, 1987

Related U.S. Application Data

[63] Continuation-in-part of Ser. No. 46,831, May 4, 1987, abandoned.

[51] Int. Cl.$^5$ .................. C07H 21/04; C12Q 1/68; G01N 33/53
[52] U.S. Cl. .................................. 536/27; 435/6; 435/172.3; 436/501; 935/78
[58] Field of Search ................ 435/6, 172.3, 34; 436/501; 536/27; 935/78

[56] References Cited

U.S. PATENT DOCUMENTS 4,302,204 11/1981 Wahl et al. .................. 23/230.3
4,468,464 8/1984 Cohen et al. ................. 435/317
4,594,318 6/1986 Gusella et al. .................. 435/6
4,623,619 11/1986 Owerbach et al. ............. 435/6

OTHER PUBLICATIONS

Wyman et al., "A highly polymorphic locus in human DNA", Proc Natl. Acad. Sci. U.S.A., 77:6754–6758 (1980).
Jeffreys et al., "Individual-specific 'fingerprints' of human DNA", Nature, 316:76–79 (1985).
Buroker et al., "A hypervariable DNA region on human chromosome 1p", Genetics, 113:PT2 (Supp. 1986).
Nakamura et al., "Characterization of a human 'midisatellite' sequence", Nucleic Acids Research, 15:2537–2547 (1987).
Litt et al., "A highly polymorphic locus in human DNA revealed by cosmid-derived probes", Proc. Natl. Acad. Sci., 82:6206–6210 (1985).
Litt et al., "A Highly Polymorphic Locus in Human DNA Revealed by Probes from Cosmid 1-5 Maps to Chromosome 2q35→37", Am. J. Hum. Genet. 38:288–296 (1986).
Bufton et al., "Four Restriction Fragment Length Polymorphisms Revealed by Probes from a Single Cosmid Map to Chromosome 19", Am J Hum Genet 38:447–460 (1986).
Buroker et al., "A Hypervariable Region at the D19S11 Locus", Human Genetics, 76:90–95 (1987).
White, R. et al., (1986) in DNA Probes, Applications in Genetic and Inf. Disease and Cancer (Ed. L. S. Lerman, Cold Spring Harbor Labs, Cold Spring Harbor, N.Y.) pp. 43–47.

Primary Examiner—Robert A. Wax
Assistant Examiner—Ardin H. Marschel
Attorney, Agent, or Firm—Klarquist, Sparkman, Campbell, Leigh & Whinston

[57] ABSTRACT

A DNA probe p13-1-25 is homologous to at least a portion of a hypervariable DNA region located on chromosome 19p13.2→19cen in the human genome. The DNA region displays extensive restrictive fragment length polymorphisms when digested with certain restriction endonucleases. Probe p13-1-25 is believed to have three closely linked lock ($\alpha$, $\phi$, $\epsilon$). Loci $\alpha$ and $\phi$ each have two common alleles, whereas $\epsilon$ has at least 33 alleles, including a null allele. Unrelated individuals display unique fragment patterns on TaqI blots probed with p13-1-25. The probe can be used to produce a genetic "fingerprint" for establishing human identity, determining engraftment of bone marrow transplants, determining parentage, and otherwise mapping genes.

9 Claims, 3 Drawing Sheets

DNA PROBE WHICH REVEALS A HYPERVARIABLE REGION ON HUMAN CHROMOSOME 19

This invention was made with government support under research which was funded in part by grant R01-GM 32500 from the National Institutes of Health. The government has rights in the invention.

CROSS REFERENCE TO RELATED APPLICATION

This is a continuation-in-part of copending U.S. patent application Ser. No. 07/046,831, filed May 4, 1987, abandoned in favor of continuing application Ser. No. 07/593,575, filed Oct. 5, 1990, and entitled "A DNA PROBE WHICH REVEALS A HYPERVARIABLE REGION ON HUMAN CHROMOSOME 1."

BACKGROUND OF THE INVENTION

1. Field of the Invention

The present invention concerns a restriction enzyme mapping probe for human chromosome 19.

2. General Discussion of the Background

Restriction fragment length polymorphisms (RFLP) are useful markers for mapping the human genome, Borstein, et al., *Am. J. Hum. Genet.*, 32:314-331 (1980). As the number of known RFLPs increases, they are becoming ever more useful in the prenatal or early diagnosis of numerous hereditary diseases. RFLPs are also used in mapping a diseased gene to a specific chromosomal location, which may serve as the first step in cloning the gene.

Diseases that have been mapped by linkage studies with RFLPs include Huntington's Disease, Gusella, et al., *Nature*, 306:234-238, (1983); Ducheene's muscular dystrophy, Murray, et al., *Nature*, 300:542-544, (1982); X-Linked Retinitis Pigmentosa, Bhattacharya, *Nature*, 309:253-255 (1984); adult polycystic kidney disease, Reeders, et al., *Nature*, 317:542-544 (1985); and cystic fibrosis, Tsui, et al., *Science*, 230:1054-1056 (1985). RFLPs also have been crucial to the elucidation of mechanisms underlying hereditary cancer syndromes frequently associated with chromosome deletions such as retinoblastoma, Cavenee, *Nature* 305:779-784 (1983), and Wilm's tumor, Koufos, et al., *Nature*, 309:170-172 (1984). In the future, RFLPs may be useful in characterizing the genetic contributions to susceptibility to common diseases which tend to cluster in families, such as colon cancer and schizophrenia, White, et al., *Nature*, 313:101-105 (1985). For example, U.S. Pat. No. 4,623,619 discloses a method of using a probe to determine the liability of human individuals to develop atherosclerosis.

RFLPs can also provide individual-specific "fingerprints" of human DNA which can be used for such forensic purposes as identification of corpses, paternity testing, and identification of rapists. For example, Jeffreys, et al. disclosed in *Nature*, 316:76-79 (1985) that simple tandem-reptitive regions of DNA ("minisatellites") which are dispersed throughout the human genome frequently show substantial length polymorphism arising from unequal exchanges which alter the number of short tandem repeats in a minisatellite. The repeat elements in a subject of human minisatellites share a common 10-15 base-pair core sequence. A hybridization probe consisting of the core repeated in tandem can detect many highly polymorphic minisatellites simultaneously to provide a set of genetic markers of general use in human linkage analysis. Certain probes can detect sets of hypervariable minisatellites to produce somatically stable DNA "fingerprints" which are completely specific to an individual (or an identical twin) and can be applied directly to problems of human identification, including parenthood testing. Unfortunately, the Jeffreys, et al., probe detects repeated sequences that occur throughout the entire human genome, and gives rise to very complex electrophoresis patterns that are sometimes difficult to interpret.

Hypervariable DNA regions have been reported near the human insulin gene (Bell, et al., *Nature*, 295:31-35 (1982)), in the $\alpha$-globin gene cluster (Higgs, et al., *Nucleic Acids Res.*, 9:4213-4224 (1981); Proudfoot, et al., *Cell*, 31:553-563 (1982); Goodbourn, et al., *Proc. Natl. Acad. Sci. USA*, 80:5022-5026 (1983)), near the c-Ha-Ras-1 oncogene (Capon, et al., *Nature*, 302:33-37 (1983)) and at the telomere of the X and Y chromosomes (Cook, et al., *Nature*, 317, 687-692 (1985)). In all cases where DNA sequence information in these regions is available, it shows that the region consists of tandemly repeated sequences which vary in copy number among chromosomes. These hypervariable regions are hypothesized to arise by mitotic or meiotic unequal crossing over or by DNA slippage during replication (Jeffreys, et al., 1985). Hypervariable regions give rise to highly polymorphic loci at numerous genomic sites. DNA probes from such regions have been useful in paternity testing and other forensic applications of well as in human gene mapping.

It is therefore a primary object of this invention to provide a DNA probe which detects a hypervariable region of a human chromosome.

Another primary object is to provide such a probe which is specific to a single human chromosome.

Yet another primary object is to provide a probe which is easy to use and gives consistent results in forensic and medical tests.

SUMMARY OF THE INVENTION

The present invention includes a DNA probe, such as p13-1-25, which is substantially homologous to at least a portion of a hypervariable DNA region located on chromosome 19p13.2→19cen in the human genome. The DNA region displays extensive restriction fragment length polymorphisms when digested with certain restriction endonucleases. When used to probe Southern blots of TaqI-digested DNA's from unrelated individuals, p13-1-25 reveals 3 to 6 hybridizing fragments, ranging in size from 3.5 too >20 kilobases (kb). Similar variation is seen with several other enzymes, including EcoRI and MspI.

A major advantage of p13-1-25 is that it detects three closely linked multiallelic loci in linkage equilibrium, which produces a very large number of possible haplotypes. The allelic fragments the probe detects cover a broad size range and are therefore easy to resolve by agarose gel electrophoresis. Probe p13-1-25 is also the only probe yet described which reveals a highly polymorphic locus on the short arm of chromosome 19. A highly polymorphic locus is deferred herein to be one having a heterozygosity in excess of about 80 percent.

The hypervariable DNA region of which probe p13-1-25 corresponds was identified by using a probe from a human genomic cosmid library. Cosmid 1-13 produced autoradiograms that indicated extensive DNA fragment size variation between unrelated individuals. Probe p13-1-25 is a single copy 2.0 kb subclone of the cosmid which has been placed in a plasmid for cloning.

The present invention includes a method of producing a genetic band pattern or "fingerprint" by digesting a human genome with a restriction endonuclease which, in combination with probe p13-1-25, produces polymorphic fragments. The fragments are then separated by agarose gel electrophoresis, partially transferred to a nitrocellulose filter, and exposed to radioactively labeled p13-1-25. The labeled probe hybridizes to fragments of DNA on the filter having homologous sequences. Autoradiographs produce a distinct band pattern which is used in human gene linkage analysis.

Probe p13-1-25 produces distinct band patterns which are characteristic of the individual from which the genome was taken. The band pattern can therefore be used for such forensic purposes as establishing the identity of a disfigured corpse or an accused assailant in a rape case. Medical applications include determining engraftment of bone marrow transplants, where it is helpful to determine if the marrow propagating in a patient's bone is diseased original tissue or healthy graft tissue. The probe can also be used to determine parentage because band patterns produced by the probes are inherited in a simple Mendelian fashion. Probe p13-1-25 is also useful in mapping genes because the probe marks a specific region on the short arm of human chromosome 19 and can monitor loss of chromosome 19 during tumorigenesis.

The foregoing and other objects, features, and advantages of the invention will become more apparent from the following detailed description of a preferred embodiment which proceeds with reference to the accompanying drawings.

DETAILED DESCRIPTION OF PREFERRED EMBODIMENT

Figure 1:
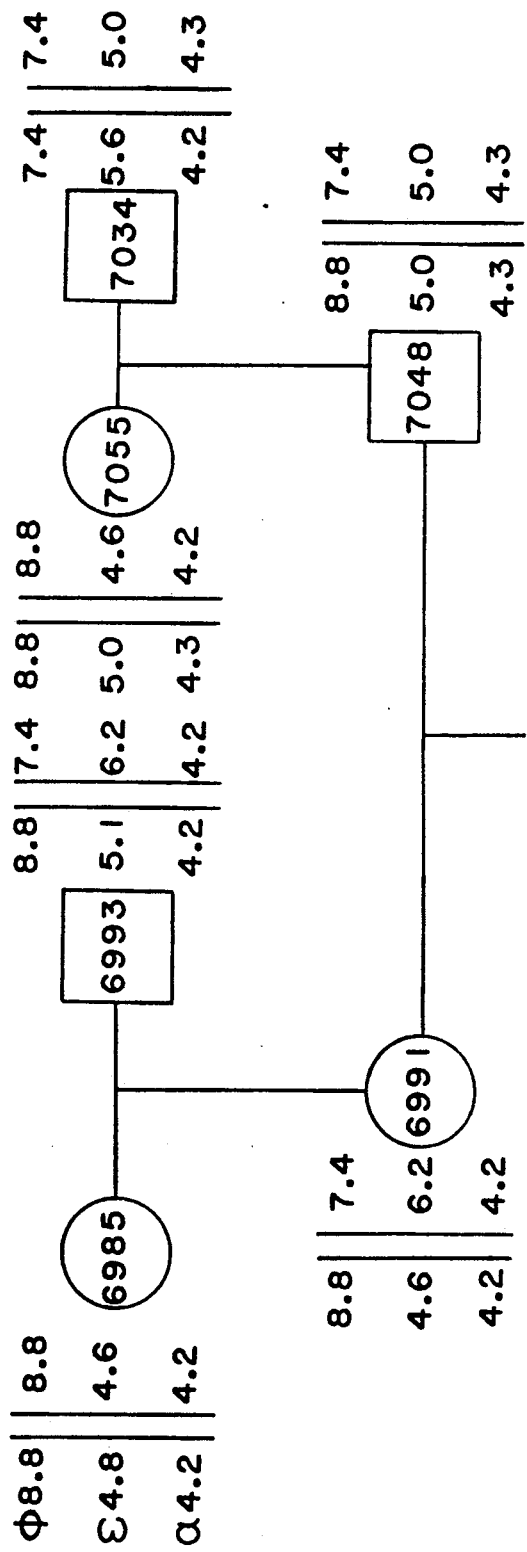
FIG. 1 is the pedigree of family K1341 which shows haplotypes, the $\phi$, $\epsilon$ and $\alpha$ loci being listed from top to bottom.
Figure 1:
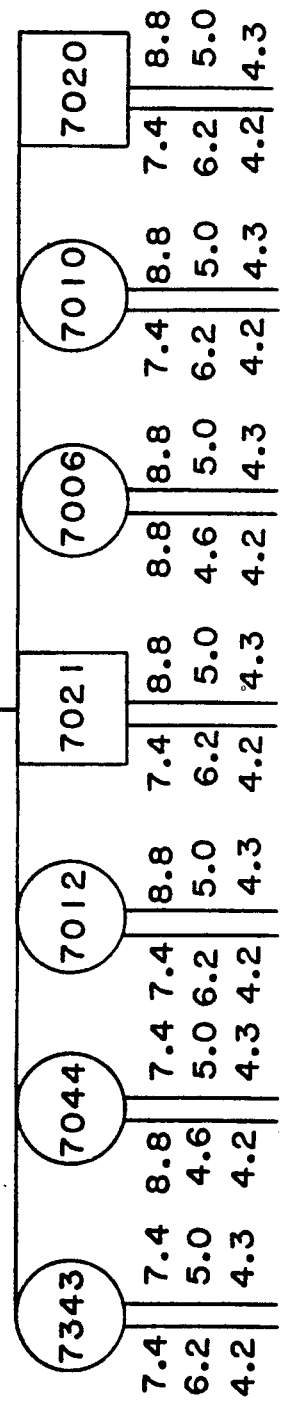

For the construction of linkage maps of human chromosomes, marker loci with multiple alleles and a polymorphism information content (PIC) near one are very useful. Botstein, et al., *Am. J. Human Genet.*, 32:314–331 (1980). Although several hundred RFLPs have been reported to date, only about 10 per cent have PIC values >0.5. Willard, et al., *Cytogenet. Cell Genet.*, 40:360–490 (1985). The present inventors have addressed this problem of RFLP's having low PICs by using a method for rapidly screening cosmids and other repeat-containing DNA clones to identify those with inserts homologous to genomic regions especially rich in RFLPs. Litt and White, *Proc. Nat'l. Acad. Sci. USA*, 82:6206–6210 (1985).

Radioactively labeled probes were prehybridized with a vast excess of nonradioactive total human DNA under conditions which drive repetitive (but not single copy) DNA into duplex form. These probes were used directly on Southern blots of restricted DNAs from panels of unrelated individuals to visualize low and single copy bands. Probes that displayed multiple polymorphisms by this method were further studied to obtain single copy subclones which revealed RFLPs. The inventors have successfully used these methods to characterize a highly polymorphic locus on chromosome 19 and isolate probe p13-1-25 which is homologous to that region. A detailed description of these methods can be found in Litt and White, *Proc. Nat. Acad. Sci. USA*, 82:6206–6210 (1985); Bufton, et al., 19 *Am. J. Human Genet.*, 38:447–460; Bufton, et al., *Hum. Genet.*, 74:425–431 (1986); Buroker, et al., *Hum. Genet.*, 72:86–94 (1986); Litt, et al.., *Hum. Genet.*, 73:340–345 (1986). Subclone (p13-1-25), which was isolated from a random human cosmid using these methods, reveals numerous insertion/deletion polymorphisms. Although the polymorphisms revealed by this probe resemble in some respects the "minisatellite" regions reported by Jeffreys, et al. (1985), they differ from minisatellites in that the sequences homologous to the probe are not dispersed throughout the genome but are tightly clustered in a specific chromosomal region, on the short arm of human chromosome 19. Probe p13-1-25 is a 2 kb segment of human chromosome 19 cloned into the BamHI site of the vector pJB8. In use, the probe is labeled with radioactive phosphorous ($^{32}$P) and hybridized with a Southern blot made from TaqI digested human DNAs. Each individual displays 3-6 hybridizing fragments ranging in size from 3.5 to >20 kb.

The inventors recently described a compound polymorphic locus (D19S11) on chromosome 19, defined by an arbitrary genomic segment cloned into a cosmid vector (Bufton et al. 1986). The polymorphic locus D19S11 consists of four closely linked RFLPs ($\alpha$, $\beta$, $\delta$, $\gamma$) on chromosome 19p13.2→19cen. The RFLPs were revealed by Southern hybridization of subclones p13-1-82 and p13-2-21 of cosmid 1-13 (cl-13) with TaqI, MspI, BamHI, and HindIII digests of human DNAs. The RFLPs have minor allele frequencies exceeding 10 percent, and seventy-two percent of unrelated individuals were heterozygous at one or more loci. Using somatic cell hybrid panels and in situ hybridization, the inventors mapped the D19S11 locus to 19p13.2→cen.

It has not been found that an additional subclone of cosmid 1-13 displays RFLPs with a high information content. Buroker et al., *Hum. Genet.*, 76:90–95 (1987). When used to probe Southern transfers of TaqI-digested DNA, this subclone, p13-1-25, reveals fragments belonging to the $\alpha$ locus seen previously with subclone p13-1-82, plus tow to four additional fragments whose sizes vary in unrelated individuals, suggesting the existence of two additional polymorphic loci. At least one of these additional loci appears to be highly polymorphic (i.e., having a heterozygosity in excess of about 80 percent), with a total of 32 different fragment sizes observed so far. Of 100 unrelated individuals tested, 98 were heterozygous at one or more of the loci revealed by this probe. Furthermore, when the sizes of TaqI fragments hybridizing to the probe in 50 of these individuals were carefully measured, no two of the individuals displayed the same set of fragments.

In 92 percent of cases, complete hydatidiform moles (CHM) arise when a single haploid sperm fertilizes an "empty ovum," and the 23,X genome duplicates to 46, XX; the remaining 8 percent of CHMs result from dispermy (Jacobs et al., *Nature*, 286:633–634 (1980)). Complete hydatidiform moles of monospermic origin are homozygous et all loci and can sometimes be used to resolve the allelic status of complex loci. The present inventors used monospermic CHMs to verify that p13-1-25 hybridized to three loci. Because of the extreme diversity of fragment sizes observed, CHMs were of limited utility for assigning alleles to loci. However, typing of several three-generation Utah kindreds with p13-1-25 allowed assignment of specific fragments to the two additional loci and suggested that they are closely linked to each other and to the α locus. In situ hybridization of p13-1-25 to a metaphase spread from an individual with a 19/X translocation with a breakpoint close to the centromere localized this probe to 19p, supporting the previous localization of D19S11 to 19p13.2→cen.

Methods of Preparing Cosmid and Subclones

Human DNA isolation from WBC, cosmid preparation and screening, subcloning, restriction mapping and hybridization procedures, somatic cell hybrid panels and in situ hybridization methods have been described in Litt and White, 1985; Bufton, et al., 1986; Buroker, et al., 1986; Litt, et al., 1986; and Bufton, et al., 1987. Southern blots used in this study were hybridized at 45°–47° and given a final wash in 0.1XSSC, 0.1 percent SDS at 65°. The somatic cell hybrid panel used in these studies has been previously described in Bufton, et al., 1986; Buroker, et al., 1986; and Litt, et al., 1986. DNAs from 3-generation Utah families were extracted from lymphoblast cell lines obtained from the Institute for Medical Research, Camden, N.J.

Subclone p13-1-25 is a 2.0-kb Sau 3A fragment of cosmid 1-13 (Bufton et al. 1986) inserted into the BamHI site of the plasmid vector pJB8 (Ish-Horowicz and Burke 1981). The insert could be excised with EcoRI, yielding fragments of 1.2, 0.54 and 0.28 kb in addition to the 5.4 kb vector fragment. For the hybridizations described herein, the entire plasmid was used as a probe. DNAs from 16 different 46,XX CHMs and lymphocytes from the parents of these models were obtained from cases collected at Magee Womens Hospital, Pittsburgh. All moles had been previously analyzed for cytogenetic heteromorphisms as well as for seven RFLPs and had been found to be homozygous at all loci tested.

Preparation and Characterization of RFLPs

A Sau3A digest of cosmid 1-13 was ligated into the BamHI site of the plasmid vector pJB8, and single-copy subclones derived from transformation of the ligation mix into E. Coli strain HB101 were screened for their ability to reveal RFLPs. When subclone p13-1-25 was used to probe Southern transfers to TaqI-digested DNAs from a panel of unrelated individuals, four to six polymorphic fragments were revealed. RFLPs revealed by subclone p13-1-25 have fragment sizes ranging from 4.2 to 12 kb. Fragments seen on other blots (not shown)- probed with p13-1-25 have ranged in size from 3.5 to >20 kb, with at least 36 different fragment sizes evident in 50 unrelated individuals studied. Similar results were obtained when Southern transfers of MspI- or EcoRI-digested DNA were probed with p13-1-25, indicating that the polymorphisms are due to insertion/deletion events rather than to single base changes affecting restriction sites.

Sizes of TaqI fragments revealed by p13-1-25 in 50 unrelated Caucasian individuals were carefully determined. The distribution of these fragment sizes, summarized in Table 1, shows that fragments of 4.2, 4.3, 7.4, and 8.8 kb each occur in at least 50 percent of the unrelated individuals sampled, with 32 additional fragment sizes occurring at lower frequencies ranging from 2 percent to 18 percent. Assignment of the 4.2- and 4.3-kb fragments to a single diallelic locus was suggested by the fact that each unrelated individual studied had one or both of these fragments. Similarly, each unrelated individual in the sample had either or both of the 7.4- and 8.8-kb fragments, suggesting that these fragments might belong to another diallelic locus. One of the individuals studied displays six TaqI fragments and is therefore heterozygous at all three loci. However the 8.8-kb allelic fragment is missing. This indicates the existence of allelic fragments in addition to the common 7.4- and 8.8-kb fragments.

TABLE 1

Sizes of TaqI fragments detected by p13-1-25. N, number of unrelated individuals in which a fragment of the indicated size was present.

| Fragment size (kb) | N |
|---|---|
| 3.5 | 1 |
| 3.7 | 2 |
| 4.2 | 45 |
| 4.3 | 25 |
| 4.5 | 4 |
| 4.6 | 1 |
| 4.7 | 7 |
| 4.8 | 2 |
| 4.9 | 3 |
| 5.0 | 5 |
| 5.1 | 9 |
| 5.2 | 1 |
| 5.3 | 1 |
| 5.4 | 5 |
| 5.5 | 6 |
| 5.8 | 5 |
| 5.9 | 2 |
| 6.0 | 3 |
| 6.1 | 5 |
| 6.2 | 7 |
| 6.6 | 2 |
| 6.8 | 3 |
| 7.0 | 4 |
| 7.2 | 1 |
| 7.4 | 32 |
| 7.5 | 1 |
| 7.7 | 1 |
| 8.0 | 5 |
| 8.2 | 4 |
| 8.3 | 3 |
| 8.4 | 2 |
| 8.8 | 33 |
| 9.5 | 3 |
| 10.7 | 2 |
| 12 | 2 |
| >20 | 2 |

The 4.2- and 4.3-kb fragments revealed by p13-1-25, but none of the other variable fragments, were also seen when subclone p13-1-82 was used to probe blots indicating that these 4.2- and 4.3-kb fragments resided at the α locus of D19S11 (Bufton et al. 1986). The presence of two to four additional fragments on blots probed with p13-1-25 suggested that this probe hybridized to two additional polymorphic loci, φ and ε, that had not been seen with any of the previously tested subclones of cosmid 1-13. The existence of these loci was confirmed by studies with complete hydatidiform moles. Southern transfers of TaqI-digested mole DNAs probed with p13-1-25 displayed three fragments, with sized consistent with the inheritance of a paternal haplotype. Because CHMs of monospermic origin are homozygous at all loci (Jacobs et al., Nature, 286:633–634 (1980)) each of the three polymorphic TaqI fragments present in a given mole must belong to a different locus. The inventors tried to exploit this property for assigning allelic fragments to loci. The results were consistent with the notion that the 7.4- and 8.8-kb fragments are allelic, since they were never present together in any of the 16 moles studied. The 7.4- and 8.8-kb fragments were provisionally assigned to the $\phi$ locus. Since 4 of the 16 complete moles examined lacked both the 7.4- and 8.8-kb fragments, it was concluded that additional alleles were also present at the $\phi$ locus. Allelism of the 7.4- and 8.8-kb fragments was confirmed by studies of several three generation Utah families described below.

Family Studies

Southern blots of TaqI-digested DNAs from three 3-generation Utah families were probed with p13-1-25. The 4.2- and 4.3-kb fragments were already assigned to the $\alpha$ locus by virtue of their hybridization with subclone p13-1-82. Therefore, only the two additional loci, $\epsilon$ and $\phi$, were considered in connection with the family studies.

In a given individual, a total of four allelic fragments was associated with the $\epsilon$ and $\phi$ loci. In the case of family K1341, the father 7048 inherited a 7.4-kb fragment from grandfather 7034 and an 8.8-kb fragment from grandmother 7055. It was therefore concluded that the remaining 5.0-kb fragment in 7048 was present in two copies (i.e., homozygous) and was assigned arbitrarily to the $\epsilon$ locus. The 7.4- and 8.8-kb fragments therefore had to be allelic, as suggested earlier, and were assigned to the 0 locus. Individuals 6993, 6991, 7044, 7012, 7021, 7010 and 7020 had both 7.4- and 8.8-kb fragments and were thus heterozygous at the $\phi$ locus. The 6.2-, 5.1-, 5.0-, and 4.6-kb fragments present in some of these individuals therefore had to be at the $\epsilon$ locus. The only fragments which could not be definitively assigned to loci in this pedigree were the 4.8- and 5.6-kb fragments, present only in grandparents and not transmitted to parents. Although in FIG. 1 these fragments are shown in the $\epsilon$ locus, one or both of them may possibly be at the $\phi$ locus.

Since the linkage phases of the alleles at the $\phi$ and $\epsilon$ loci in the parents of K1341 could be determined, it was possible to show that all of the seven children typed were nonrecombinants for this pair of loci, and the LOD scores calculated for zero recombination fraction. LOD scores were also obtained for two other phase-known Utah pedigrees, and the family data is summarized in Table 2, which is a linkage study for $\alpha$, $\epsilon$, and $\phi$ loci of D19S11. The LOD score at zero recombination observed for each pair of loci in each family studied is shown in Table 2. NI indicates that the data was not informative.

TABLE 2

| Family loci | K1329A | K1331 | D1341 | Total |
|---|---|---|---|---|
| α-ε | 2.1 | 2.7 | NI | 4.8 |
| α-φ | 2.1 | 1.2 | NI | 3.3 |
| ε-φ | 2.1 | 1.2 | 2.1 | 5.4 |

TaqI fragments of 7.4 and 8.8 kb, assigned to the $\phi$ locus in K1341, were also seen in the two additional families 1329A and 1331. To calculate LOD scores, it was assumed that these fragments were also at the $\phi$ locus in these families.

Among at least eleven informative children, no recombinants were observed for any of the three pairs of loci. LOD scores exceeding 3.0 at zero recombination for all three pairs of loci provide strong support for close linkage of the three loci and provide the basis for assigning the $\epsilon$ and $\phi$ loci to D19S11.

Figure 2:
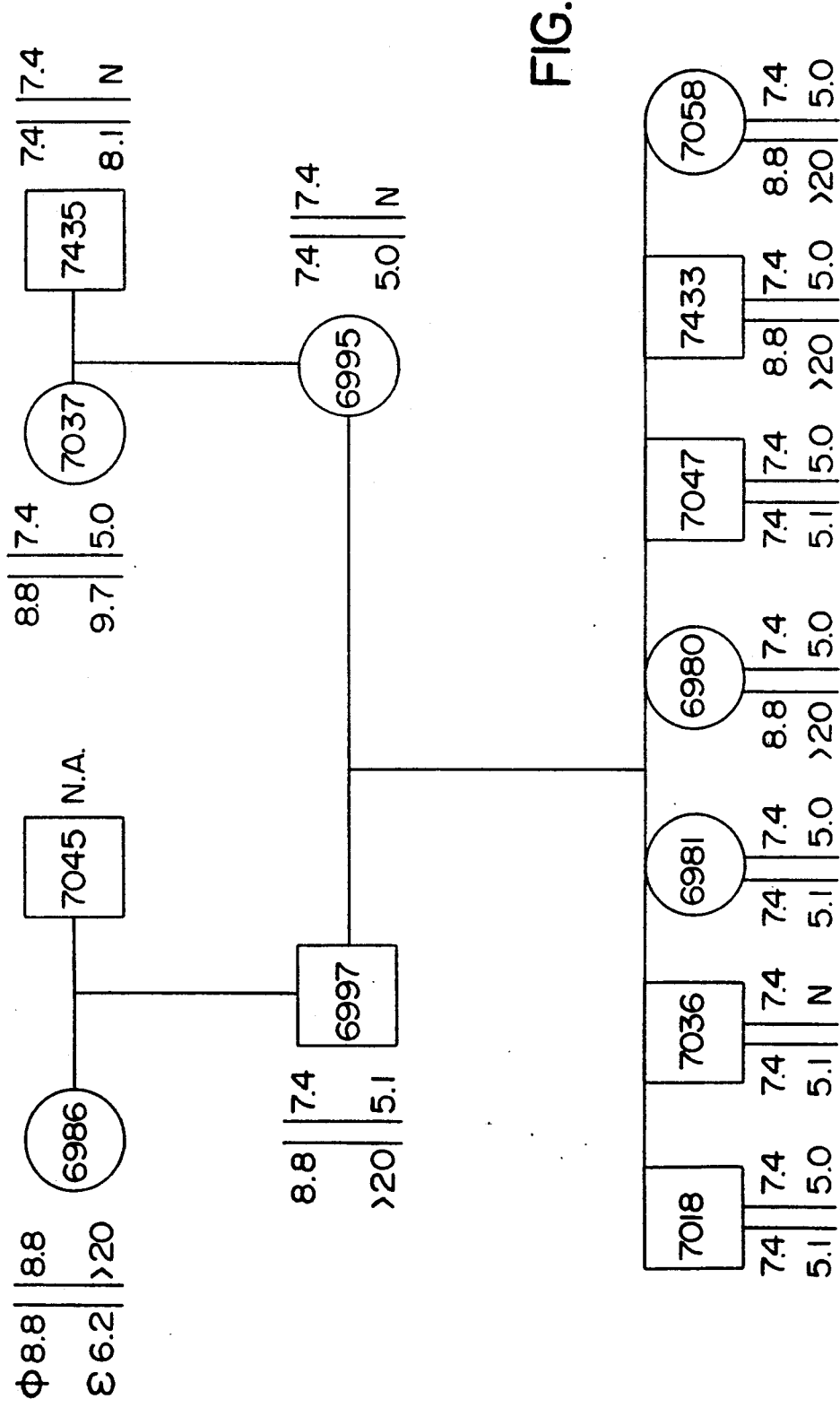
FIG. 2 is the pedigree of family K1329A, two-locus haplotypes being shown for each family member for the $\phi$ (upper) and $\epsilon$ (lower) loci.

The results of typing kindred K1329A with p13-1-25 at the $\epsilon$ and $\phi$ loci suggested that existence of a null allele at the $\epsilon$ locus (FIG. 2). The pedigree of K1329A is shown in FIG. 2, where two locus haplotypes are shown for each family member for the $\phi$ (upper) and $\epsilon$ (lower) loci. The designation ">20" in FIG. 2 represents a TaqI fragment of size greater than 20 kb which could not be accurately sized because the largest standard on the Southern blot used was 18.5 kb. "N" represents a null allele which is believed to be segregating in this family.

Aside form the $\alpha$-locus fragments, the grandfather 7435 had only two different TaqI fragments of 8.1 and 7.4 kb; he was initially considered homozygous at both the $\epsilon$ and the $\phi$ loci. However, this assumption was inconsistent with the observation that 7435 transmitted only the 7.4-kb fragment to his daughter 6995. Similarly, 6995 had only two different non-$\alpha$ locus TaqI fragments and had transmitted only the 7.4-kb fragment to her son 7036. To explain these results, the inventors propose that a null allele is segregating in this family. Such a null allele might consist of a low molecular weight fragment which ran off the gel and was not detected. Alternatively, a null allele might signify deletion of the entire $\epsilon$ locus-region of homology to probe p13-1-25. Similar evidence for null alleles was obtained in four additional three-generation Utah families (data not shown).

Substantially Identical and Homologous Probes

The present invention includes DNA probes which contain a sequence substantially identical to or homologous with the base pair sequence of probe p13-1-25. A substantially homologous sequence is one in which a high degree of homology between the sequences of two or more DNA molecules can be tested for by determining whether the DNA molecules in question hybridize to each other under stringent conditions, such as those set forth in Bethesda Research Laboratories, *DNA Detection System Instruction Manual* (Catalogue No. 8239SA), pp. 8–9 (1984). See also Leary et al., *Proc. Natl. Acad. Sci. USA*, 80:4045–4049 (1983), modifying the procedures of Wahl, et al., *Proc. Natl. Acad. Sci. USA*, 76:3683–3687 (1979).

In Situ Hybridization

In situ hybridization of p13-1-25 to a metaphase spread from an individual with a 19/X translocation showed localization to 19p13.2. A representative metaphase was R-banded following hybridization. The same metaphase was destained and restained with Wright's stain to show silver grains.

In situ hybridization was performed with metaphase spreads from a female with a balanced reciprocal X/19 translocation [46.X.t(X;19)(19pter→cen→Xqter; Xpter=cen→19qter)]. Chromosome identification and silver grain localization were made by a combination of bright filed and fluorescent microscopy. Fluorescent R-banding (Schweizer, *Cytogenet Cell Genet.,* 27:190–193 (1980)) was used for chromosome identification, while standard Wright's stain was used for making a photographic record of grain location. Techniques for labeling probes and conditions for hybridization with metaphase spreads have been previously described (Bufton et al. 1986).

Figure 3:
FIG. 3 is a histogram of chromosomal distribution of silver grains from in situ hybridization of probe p13-1-25 to chromosomes of a 19/X translocation carrier.

FIG. 3 is a histogram of chromosomal distribution of silver grains from in situ hybridization of probe p13-1-25 to chromosomes of the 19/X translocation carrier. It summarizes the results of scoring 100 labeled metaphases. There was significant label on the short arm of the normal 19 as well as on the 19 short arm involved in the 19/X translocation (10 percent and 16 percent respectively). The proximal portion of 19p was more heavily labeled than the distal region. However, due to the small size of the short arm of 19 and the grain scatter, more precise localization was not possible. Previous studies of probe p13-1-82 with a somatic cell hybrid panel consisting of several cell lines containing different regions of chromosome 19 indicate that the $\alpha$ locus, and presumably the closely linked $\phi$ and $\epsilon$ loci, are proximal to 19p13.2 (Bufton et al. 1986).

The hypervariable region at the D19S11 locus is detected by probe p13-1-25 and apparently localized to the short arm of human chromosome 19. Although not desiring to be bound by theory, the present inventors believe that variations in the copy number of short repeated sequences may be responsible for the extensive polymorphism revealed by p13-1-25, as has been found in the case of minisatellites (Jeffreys, et al., 1985).

Probe Structure and Uses

The inventors have previously described a set of three closely linked insertion/deletion RFLPs ($\alpha$, $\phi$ and $\epsilon$) on the short arm of chromosome 19 detected by p13-1-25, a single-copy 2.0-kb subclone of cosmid 1-13. These closely linked RFLPs were described in Bufton et al., *Am. J. Hum. Genet.*, 38:447–460 (1986), which is incorporated herein by reference. All allelic fragments observed are larger than the 2.0 kb insert of the probe, and no constant fragments are observed. These observations suggest that the probe is homologous to a triplicated region. The $\alpha$ and $\phi$ loci each have two frequent alleles, while the $\epsilon$ locus has at least 30 alleles with frequencies ranging from 0.5 percent to 4.5 percent. Close linkage of the three loci is indicated by family studies and supported by the existence of only a single site of in situ hybridization at 19p13.2→cen, the same location previously found for another subclone (p13-1-82) of the same cosmid. Use of probe p13-1-25, which identifies the $\phi$ and $\epsilon$ loci, will insure that nearly all families are informative at the D19S11 locus, increasing its usefulness for mapping genes located in the proximal region of the short arm of chromosome 19.

Among 100 unrelated individuals types with p13-1-25, there were 98 who were heterozygous at one or more of the three loci which it reveals, making this probe a particularly useful tool for monitoring reduction to homozygosity of chromosome 19 markers consequent upon loss of the chromosome during tumorigenesis. Also, p13-1-25 may be useful for following the course of engraftment of donor bone marrow after transplantation (Blazar et al. 1985). In a recent series, 30 of 33 donor-recipient sib pairs were informative with this probe.

The DNA fingerprints produced by probe p13-1-25 are sufficiently stable and individual-specific for use in human identification in, for example, forensic medicine. Badly disfigured corpses can be identified by preparing a genetic fingerprint with probe p13-1-25, and comparing the fingerprint to bands produced by DNA of a previously collected tissue sample from a known individual who is believed to be the corpse. If the band patterns match, identity has probably been established. Rapists can similarly be identified by comparing the band patterns from semen in the victim with the band patterns produced by the DNA of an individual suspected of committing the crime.

The simple Mendelian inheritance of band patterns produced by p13-1-25 makes it possible to use the probe in determining parentage, for example, in a disputed paternity suite, Approximately half of the polymorphic fragments in an offspring are derived from the father, and there paternal fragments can be identified by comparison of the mother's and offspring's DNA band patterns. All fragments present in the offspring but not in the mother must be present in the father (allowing for a possible rare new mutation). The probe produces at least 36 fragments, many of which are polymorphic. The large number of polymorphic fragments makes it possible not only to exclude paternity, if bands are present in the offspring but not the mother or putative father, but also t predict statistically the possibility of inclusion of paternity. The large number of polymorphic fragments produced by the probe provides a high statistical likelihood of inclusion of paternity.

The highly polymorphic nature of the hypervariable region D19S11 also makes p13-1-25 a potentially useful tool for following engraftment of donor bone marrow after transplantation (Blazar, et al., *Blood*, 66:1436–1444 (1985)), and for many forensic applications. Furthermore, p13-1-25 might be useful in isolating genomic clones capable of revealing additional hypervariable regions.

Restriction Enzyme Mapping

Probe p13-1-25 can also be used to map genes on chromosomes using the techniques disclosed by Gusella, et al. (1983), Murray, et al. (1982), Bhattacharya, et al. (1984), Reeders, et al. (1985) or Tsui, et al. (1985). A disease gene can be located by using the knowledge that a RFLP closely linked to a gene would be inherited with that gene. The inheritance of numerous RFLPs in families having the disease can be traced using random cloned DNA fragments from a human gene library as probes. An RFLP which is found to be inherited along with the disease indicates that the RFLP and disease gene are closely linked. Probe p13-1-25 will therefore indicate the presence of a disease gene on the short arm of human chromosome 19.

ATCC Deposit

Probe p13-1-25 has been deposited with American Type Culture Collection in Rockville, Md., and assigned ATCC accession No. 40329. The deposited probe is a plasmid containing an insert DNA from cosmid 1-5. In use, the probe would be amplified through bacterial transformation to produce a bacterial colony. The plasmid would then be isolated and labeled, for example, with radioactive phosphorous.

Having illustrated and described the principles of the invention in a preferred embodiment, it should be apparent to those skilled in the art that the invention can be modified in arrangement and detail without departing from such principles. We claim all modifications coming within the spirit and scope of the following claims.

We claim:

1. A plasmid having ATCC accession No. 40329 which contains a clone of DNA probe p13-1-25.

2. A DNA probe containing a sequence of the inserted DNA of a plasmid having ATCC accession No.

40329, which insert hybridizes to the locus D19S11 of the human genome, the sequence including a sufficient number of bases that, when the probe is hybridized to polymorphic fragments which are obtained by digesting the D19S11 locus of a human genome and which are separated by Southern blotting, the resulting blot has a distinctive band pattern that is characteristic of the individual from which the genome was taken.

3. The probe of claim 2 further comprising a label which enables detection of the probe.

4. A recombinant DNA molecule comprising a DNA segment containing a sequence from the base sequence of probe p13-1-25 and which hybridizes to locus D19S11, a highly polymorphic locus on the short arm of chromosome 19 of a human genome, the sequence including a sufficient number of bases that, when the molecule is hybridized to polymorphic fragments which are obtained by digesting the D19S11 locus of a human genome and which are separated by Southern blotting, the resulting blot has a distinctive band pattern that is characteristic of the individual from which the genome was taken.

5. The molecule of claim 4 that is a plasmid.

6. The DNA probe having a sequence which hybridizes to at least a portion of locus D19S11, a highly polymorphic locus on the short arm of chromosome 19 of a human genome, and which reveals 3 to 6 hybridizing fragments ranging in size from 3.5 to greater than 20 kilobases when used to probe Taq I digested DNA from the D19S11 locus, the sequence including a sufficient number of bases that, when the probe is hybridized to polymorphic fragments obtained by digesting the D19S11 locus of a human genome and which are separated by Southern blotting, the resulting blot has a distinctive band pattern that is characteristic of the individual from which the genome was taken.

7. The probe of claim 3 wherein the label is a radioactive material.

8. The probe of claim 7 wherein the radioactive material is phosphorous.

9. The probe of claim 4 further comprising a label for detecting the sequence.

* * * * *